US012636462B2

(12) United States Patent
Falck et al.

(10) Patent No.: US 12,636,462 B2
(45) Date of Patent: May 26, 2026

(54) LIGHT THERAPY SYSTEM AND METHOD

(71) Applicant: KONINKLIJKE PHILIPS N.V., Eindhoven (NL)

(72) Inventors: Thomas Maria Falck, Aachen (DE); Antonius Fredericus Maria Dieu-donné Akkermans, Waalre (NL)

(73) Assignee: Koninklijke Philips N.V., Eindhoven (NL)

( * ) Notice: Subject to any disclaimer, the term of this patent is extended or adjusted under 35 U.S.C. 154(b) by 1074 days.

(21) Appl. No.: 16/607,951

(22) PCT Filed: Apr. 16, 2018

(86) PCT No.: PCT/EP2018/059621
§ 371 (c)(1),
(2) Date: Oct. 24, 2019

(87) PCT Pub. No.: WO2018/197243
PCT Pub. Date: Nov. 1, 2018

(65) Prior Publication Data
US 2024/0216641 A1 Jul. 4, 2024

(30) Foreign Application Priority Data
Apr. 24, 2017 (EP) ..................................... 17167766

(51) Int. Cl.
*A61M 21/00* (2006.01)

(52) U.S. Cl.
CPC ..... *A61M 21/00* (2013.01); *A61M 2021/0044* (2013.01)

(58) Field of Classification Search
CPC .......... A61M 21/00; A61M 2021/0044; A61M 2021/0005; A61M 21/02; A61N 5/0613; A61N 5/0618; A61N 5/622
See application file for complete search history.

(56) References Cited

U.S. PATENT DOCUMENTS

| | | | |
|---|---|---|---|
| 10,257,902 B2 | 4/2019 | Trouwborst et al. | |
| 2006/0009822 A1* | 1/2006 | Savage ................. | A61M 21/00 |
| | | | 607/88 |

(Continued)

FOREIGN PATENT DOCUMENTS

| | | |
|---|---|---|
| CA | 2829054 A1 | 10/2012 |
| EP | 2796166 A1 | 10/2014 |

(Continued)

OTHER PUBLICATIONS

Ono, H. et al., "The usefulness of bright light therapy for patients after oesophagectomy", Intensive and Critical Care Nursing (2011) 27, 158-166.

(Continued)

*Primary Examiner* — Alex M Valvis
*Assistant Examiner* — Julie Thi Tran

(57) ABSTRACT

A light therapy system (12) for administering a controllable melanopic luminous exposure includes a lighting assembly (16) for producing a light output (68) having a configurable illuminance and color temperature. Based on a received target melanopic luminous exposure a controller (24) of the system constructs a suitable control schedule (71) for controlling parameter levels of the lighting assembly over time such that in total over a defined treatment period (78), the indicated target melanopic luminous exposure is delivered. In constructing the control schedule, the relative melanopic sensitivity of humans to light of different color temperatures is taken into account. The color temperature of the administered light is accordingly controlled such that after adjusting for color, the delivered luminous exposure conforms to the input exposure target.

20 Claims, 4 Drawing Sheets

(56) References Cited

U.S. PATENT DOCUMENTS

| 2012/0215290 A1* | 8/2012 | Chen | A61N 5/0618 |
| | | | 607/90 |
| 2013/0293144 A1* | 11/2013 | Tomiyama | H05B 45/24 |
| | | | 315/294 |
| 2014/0052220 A1* | 2/2014 | Pedersen | A61M 21/00 |
| | | | 607/88 |
| 2015/0035440 A1* | 2/2015 | Spero | F21S 41/147 |
| | | | 315/153 |
| 2015/0126806 A1* | 5/2015 | Barroso | H05B 47/11 |
| | | | 315/153 |
| 2016/0129280 A1* | 5/2016 | Douglas | H05B 47/19 |
| | | | 607/88 |

FOREIGN PATENT DOCUMENTS

| WO | 2013175348 A1 | 11/2013 | |
| WO | WO-2017192566 A1* | 11/2017 | A01G 7/045 |
| WO | WO-2021163343 A2* | 8/2021 | H05B 47/165 |

OTHER PUBLICATIONS

International Search Report and Written Opinion, International Application No. PCT/EP2018/059621, Mailed on Jun. 11, 2018.
DIN SPEC 5031-100, Aug. 2015.

\* cited by examiner

LIGHT THERAPY SYSTEM AND METHOD

This application is the U.S. National Phase application under 35 U.S.C. § 371 of International Application No. PCT/EP2018/059621, filed on 16 Apr. 2018, which claims the benefit of European Application Serial No. 17167766.9, filed 24 Apr. 2017. These applications are hereby incorporated by reference herein.

FIELD OF THE INVENTION

This invention relates to a light therapy system and method.

BACKGROUND OF THE INVENTION

It is known that many patients treated in a clinical unit, for example a hospital, and in particular an intensive care unit (ICU), can exhibit a disturbance of their sleeping cycle. This can hamper the healing process of the patient and in particular can increase their risk of developing delirium. Up to 80% of critically ill patients suffer from delirium, resulting in an increased length of stay and in some cases even an increased mortality rate. For this reason, recent guidelines published by critical care societies, namely in the USA and Germany, propose means for prevention of delirium in such patients. The means proposed in particular are non-pharmacological, focusing instead upon attempts to naturally restore the circadian rhythms of patients through bright light therapy.

For humans, exposure of the eyes to light is the most significant factor in synchronizing the circadian rhythm to the natural 24-hour day/night cycle. It is known that by exposing a patient to specially tailored cycles of bright light, synchronized with the cycles of the sun, their circadian rhythm can be re-calibrated and sleep disturbance reduced.

US 2015/0126806 A1 discloses a lighting system for controlling lighting conditions in a room in accordance with a pre-determined schedule, and in particular in accordance with a circadian rhythm schedule, so as to reduce delirium in a patient. The system includes means for controlling internal light sources and also the amount of external light entering a room in order to adjust the light level or light intensity in the room. The system also comprises light sensors to detect the amount of light that a patient is exposed to.

Developments in light therapy systems for improving sleep patterns in patients are generally sought.

SUMMARY OF THE INVENTION

The invention is defined by the claims.

According to an aspect of the invention, there is provided a light therapy system, comprising:

a lighting assembly operable to create a light output having a controllable illuminance and color temperature; and a controller, operatively coupled to the lighting assembly, and adapted to:

receive a data input indicating a target melanopic luminous exposure for administration by the lighting assembly;

retrieve from a data store one or more melanopic weighting factors corresponding to a relative melanopic effect of different color temperatures of light;

create, based on the melanopic weighting factors, a control schedule for controlling the illuminance and color temperature values of the lighting assembly over time such as to deliver in total over a defined treatment period the target melanopic luminous exposure; and control the lighting assembly in accordance with the control schedule.

Embodiments of the invention enable a dedicated light therapy program to be created for a given patient and configured to deliver a specified target melanopic luminous exposure. A controller of the light therapy system creates a control schedule for controlling illuminance and color temperature of a lighting assembly over time such that over the course of a particular time window (the treatment period) the target luminous exposure is delivered.

The target melanopic luminous exposure may for instance be specified by a clinician. The system can hence enable highly efficient technical implementation of a light therapy treatment, based on only minimal input from a clinician. Although systems for delivering light therapy are known, systems configured to generate a custom light therapy program for a particular patient, based only upon a specific target melanopic luminous exposure are not found in the art. This system hence has the potential to significantly improve the efficiency in management and delivery of these light-based treatments for improving sleep and reducing delirium.

Melanopic luminous exposure is a term of the art and corresponds to a dosage of light delivered to a patient, equal to the product of the illuminance of the light and the time period over which it is delivered. It is typically measured in units of Lux Hours (Lux being the SI unit of illuminance). For brevity, in descriptions which follow, melanopic luminous exposure may be shorted simply to 'luminous exposure'. Unless stated otherwise, references to 'luminous exposure' should be read as referring to 'melanopic luminous exposure' as defined above.

The system of the present invention is further distinguished over the prior art, among other things, in being configured to explicitly take account of the color temperature of the light delivered to the patient. It has recently been discovered that the biological effect of the light, in terms of its relative impact on the human circadian cycle (known as "melanopic effect") is dependent upon the color temperature of the light. Accordingly, the inventors of the present invention have determined a set of melanopic weighting factors quantifying this relative biological effect of different color temperatures of light in a manner which can be readily utilized by a technical system in creating a light therapy schedule. Accordingly, 'melanopic luminous exposure' for the purposes of the present disclosure should be understood as referring to the color temperature weighted melanopic luminous exposure (the melanopic luminous exposure in lux hours further adjusted for the relative melanopic or biological sensitivity of humans to light of different color temperatures).

The controller of the system is adapted to retrieve the set of relative weighting factors from an associated data store and to accordingly set intensity and color temperature values of the light output within the control schedule such that throughout the duration of the treatment period, the target melanopic luminous exposure is delivered.

Creating a lighting schedule for reducing delirium in which melanopic effect of the color temperature of the light is taken into account represents a significant departure from known systems in the art. Not only is color temperature taken into account, the system includes a lighting assembly in which the color temperature is controllable. The controller is therefore able to configure color temperature as one of a plurality of variable parameters in the control schedule. In certain embodiments for instance, a user may specify a preferred color temperature, and a control schedule may then be determined such as to include light of that color while still ensuring delivery of the specific target melanopic luminous exposure.

In particular, the controller may be adapted to receive color preference data indicating one or more preferred color temperature values, and to create the control schedule such that the color temperature of the light output, for at least a portion of the treatment period, has the preferred color temperature value.

Accordingly, these embodiments are able to provide efficient technical implementation of a light output therapy which delivers a required melanopic luminous exposure, while allowing a greater degree of configurability over color temperature, without impacting on the accuracy of the light dosage delivered. This offers greater choice to patients and users of the system who may prefer light of certain color temperatures, and also offers greater flexibility to clinicians in configuring the light treatment.

To improve efficiency in creating a control schedule, the control schedule may be based on a pre-stored schedule template. The template may include a fixed temporal portion and a configurable temporal portion, where the controller is adapted to determine the configurable portion such that the two portions together deliver the target melanopic luminous exposure. By temporal portion is meant a portion of the schedule corresponding to one or more particular time periods within the overall treatment period. By 'fixed' is meant a pre-determined portion wherein at least a general trend or pattern of the illuminance values over that time period are pre-determined and not altered or configured by the controller. The relative overall lengths of the fixed temporal portion and the configurable temporal portion may be configurable. The fixed temporal portion may be formed of a plurality of sub-portions which are temporally discontinuous.

By way of example, the pre-stored schedule template may have a beginning portion and an end portion which are fixed, and a central portion which is configurable. The beginning and end portion together form the fixed temporal portion of the template. Preferably the beginning and end portion might each be shorter in length than the central portion.

In accordance with one or more embodiments, the controller may be adapted to create the control schedule such that an average illuminance level during the configurable temporal portion is greater than an average illuminance level during the fixed temporal portion. The fixed temporal portion may for instance provide a relatively low-level baseline illuminance, while the configurable portion provides the substantive part of the overall luminous exposure delivered. This higher level portion may in examples to follow be termed a 'boost' portion.

According to one or more embodiments, the pre-stored template may include a plurality of configurable temporal portions, being separated by a plurality of intermediate fixed temporal portions. The variations and options described above in relation to the pre-stored template may also be applied to examples of this embodiment.

As noted above, embodiments of the invention offer improved configurability of the light therapy program delivered to patients. Various parameters of the treatment schedule may be defined or constrained either in accordance with pre-stored settings or by a clinician, other user or even a patient. The controller may be configured to determine a suitable control schedule for delivering the target melanopic exposure while conforming to such defined constraints or parameters.

In accordance with one or more embodiments for instance, the controller may be adapted to further retrieve from a data store an indication of an upper and lower limit for the illuminance of the light output during the treatment period and an indication of an upper and lower limit for a duration of at least a configurable temporal portion of the treatment period, and to create at least a configurable portion of the control schedule in accordance with said values. The limits may be pre-set in the data store, or may be stored by a clinician or other user.

It may be advantageous for instance for a clinician to be able to set boundary levels for various parameters, in this case illuminance and duration of at least a configurable portion of the control schedule. This may in examples be for clinical reasons, or simply for reasons of practicality or patient preference.

The light therapy system may further comprise a user input device for receiving the data input indicating the target melanopic luminous exposure and a user output device, and wherein, in advance of receiving the target melanopic luminous exposure, the controller is adapted to: determine, based upon the upper and lower limits for the illuminance and duration values, a maximum and minimum melanopic luminous exposure deliverable using the lighting assembly for each of a set of light color temperatures; and control the user output device to communicate said determined upper and lower limits for each color temperature.

According to these examples, the controller calculates, based on the constraints retrieved from the data store what is the maximum and the minimum total luminous exposure that can be administered by the system were the light output to be set statically at each of a range of different color temperatures. Since the biological effect of different color temperatures of light is different, a light output at some color temperatures will be able to deliver a greater total luminous exposure than others.

The calculated maxima and minima are communicated to a user of the system (e.g. a clinician) via a user output device. By way of example, this may be a display, though other user output devices will of course be immediately apparent to the skilled person. By thus communicating the upper and lower deliverable light dosages, clinical decision making by the clinician may be informed by certain technical limitations of the system. Time may thus be saved by informing the clinician in advance of what luminous exposures are in fact possible, or at least what light color temperature(s) the patient will be limited to should certain luminous exposures be requested.

In some cases, the communicated range of possible luminous exposures may exclude the exposure dose which a clinician deems necessary for the patient. In this case, the clinician might alter the stored upper and lower limits for duration or illuminance referred to above (in cases where the system is configured to allow adjustment of these values).

After communicating the calculated maxima and minima for deliverable luminous exposures for each color temperature, the controller may wait to receive a target melanopic luminous exposure input by the user or clinician using the user input device. After receipt of the target melanopic luminous exposure, the controller may be further adapted to: determine, based on the upper and lower limits for duration and illuminance, a maximum and minimum value of at least one of the following parameters sufficient to deliver the target melanopic luminous exposure:

color temperature of the light output during at least a
configurable temporal portion of the control schedule;

duration of at least a configurable temporal portion of the
control schedule; and illuminance level of the light output during at least a
controllable temporal portion of the control schedule.

The controller may then control the user output device to
communicate the determined maximum and minimum values; receive from the user input a data input indicating a
preferred value for one or more of said parameters; and
create the control schedule such that the light output, for at
least a portion of the treatment period, is consistent with said
preferred values.

Examples in accordance with these embodiments hence
calculate and provide additional information to a clinician or
user which may help to inform decision-making regarding
the therapy. This may be decision-making as to clinically
important elements of the delivered treatment (such as
duration of the treatment) or simply decisions as to personal
preference (such as in some cases color temperature of the
light, which might be chosen by a patient according to
preference). Maxima and minima of more than one of the
listed parameters may be communicated.

The controller may in some examples wait to receive
input of a desired value or range for one or more of the above
parameters, and subsequently re-calculate achievable
maxima and minima for the remaining parameters (if applicable). These may then be re-communicated to the user
(such as a clinician) via the user output. The controller may
then again wait for input of a specified value or range of one
of the displayed parameters. This process may continue until
all parameters of the therapy have been set.

In the above embodiments, reference is made to retrieving
data, settings or parameters from a data store. The data store
may in examples be comprised by the controller, may be a
separate component comprised by the system, or may be
external to the claimed system and but communicably linked
to the controller. There may be more than one data store.

In accordance with any embodiment, the lighting assembly of the system may comprise a plurality of light sources
each having a respective spectral emission profile, and
wherein control of the color temperature of the light output
comprises determining, based on pre-stored configuration
data, light levels for each of said plurality of light sources.
The pre-stored configuration data may be stored in a data
store and retrieved by the controller. The data store may be
local to the system or remote from the system.

The configuration data by way of example may include a
look-up table or other data structure in which are stored, for
each of a range of possible color temperatures, the necessary
operating settings or output settings for each of the light
sources in order to create light of the given color. When a
light color is specified, this table or other data structure may
be consulted and the indicated settings for each light source
implemented.

Light delivered to a patient as part of a light treatment
therapy will only have an effect on the circadian rhythm if
it is actually received by the photoreceptors in the eye.
Accordingly, the actual biological effect of a delivered light
treatment will depend upon the proportion of time over the
treatment period that the eyes of the subject remain open.

In accordance with one or more embodiments therefore,
the system may further comprise an eye status sensor for
detecting whether eyes of a user are open or closed, the
sensor being operatively coupled with the controller, and the
controller being adapted to adjust a duration of, and/or the
illuminance and/or color temperature of, the light output during at least a configurable temporal portion of the control
schedule based on readings from the sensor in order to
ensure delivery of the target luminous exposure.

The eye status sensor may be an optical sensor such as a
camera, or may be any other sensor suitable for sensing, or
providing an indication of, when an eye or eyes of a user are
open and/or closed. The controller may be configured to
implement a feedback loop, wherein, based upon sensor
readings, the control schedule is modified so as to counter
any reductions in the actual optical exposure of the patient
to the delivered light output. The control schedule may
hence be altered (for instance the treatment extended or
increased) such that the remaining scheduled light exposure
is sufficient to deliver the target light exposure.

The controller may for example calculate, based on readings from the eye status sensor over a defined sensing
period, an aggregate time period for which a user's eyes
have been closed, and to extend the duration of at least a
temporal portion of the control schedule by said aggregate
time period.

Additionally or alternatively, the system of the invention
may comprise a presence sensor, operatively coupled with
the controller and arranged in use to detect the presence or
absence of a user within a light path of the lighting assembly,
and wherein the controller is adapted to adjust a duration of,
and/or the illuminance and/or color temperature of the light
output during at least a configurable temporal portion of the
control schedule based on readings from the sensor in order
to ensure delivery of the target melanopic luminous exposure. This option is based upon the same principle: the
generated light can only have the necessary biological effect
for the period that the patient is actually present.

To improve the accuracy of the delivered luminous exposure dose, the system may further comprise a light level
sensor, arranged to detect a light level proximal to a user, and
wherein the controller is adapted to adjust a duration of,
and/or the illuminance and/or color temperature of, the light
output during at least a configurable temporal portion of the
control schedule based on readings from the sensor, in order
to ensure delivery of the target luminous exposure.

Optionally, the light level sensor may be arranged proximal to a user's eye or eyes.

Based on readings from the light level sensor, the controller may determine the actual illuminance of the light
received at the location of the patient. Should the measured
illuminance be lower than expected, the illuminance level of
the lighting assembly may be increased to compensate, and
vice versa in the case that the measured illuminance is higher
than expected. In this way a desired melanopic luminous
exposure may be more reliably administered.

In addition to the opening and closing of a patient's eyes,
the transmittance of the eye lens itself affects the amount of
light which is received by a patient. Transmittance of the eye
lens tends to decrease with increasing age. Accordingly, in
accordance with one or more embodiments, the controller
may be further adapted to:

retrieve from a data store an indication of an age of a user;

retrieve from a data store a set of age weighting factors,
being based on average sensitivity to light of users of
different ages; and adjust a duration of, and/or the illuminance and/or color
temperature of the light output during at least a configurable temporal portion of the control schedule
based on retrieved age and weighting factors in order to
ensure delivery of the target luminous exposure.

Examples in accordance with a further aspect of the
invention provide a light therapy method comprising controlling a lighting assembly to deliver a target melanopic luminous exposure, the lighting assembly being operable to create a light output having a controllable illuminance and color temperature, and the method comprising:

receiving a data input indicating a target melanopic luminous exposure for administration by the lighting assembly;

retrieving from a data store one or more melanopic weighting factors corresponding to a relative melanopic effect of different color temperatures of light;

creating, based on the melanopic weighting factors, a control schedule for controlling the illuminance and color temperature values of the lighting assembly over time such as to deliver in total over a defined treatment period the target melanopic luminous exposure; and controlling the lighting assembly in accordance with the control schedule.

BRIEF DESCRIPTION OF THE DRAWINGS

Examples of the invention will now be described in detail with reference to the accompanying drawings, in which.

DETAILED DESCRIPTION OF THE EMBODIMENTS

A light therapy system for administering a controllable melanopic luminous exposure includes a lighting assembly for producing a light output having a configurable illuminance and color temperature. Based on a received target melanopic luminous exposure a controller of the system constructs a suitable control schedule for controlling parameter levels of the lighting assembly over time such that in total over a defined treatment period, the indicated target melanopic luminous exposure is delivered. In constructing the control schedule, the relative melanopic sensitivity of humans to light of different color temperatures is taken into account. The color temperature of the administered light is accordingly controlled such that after adjusting for color, the delivered luminous exposure conforms to the input target luminous exposure.

A preferred embodiment of the invention will now be described in detail with reference to FIGS. 1 to 7.

Lighting systems in patient rooms are often designed more around the functionality of the light for caregivers than the clinical effect of the light upon (in particular the circadian rhythm of) patients. The present invention aims to redress this problem.

The system of the present invention allows clinicians to specify a desired melanopic luminous exposure to be administered to a given patient, with the system configured to ensure that the patient receives the prescribed dosage of light. To this end, in accordance with a preferred set of embodiments, the system at first calculates, based on the clinician's prescription and the characteristics of the used lighting assembly, a tailored light therapy schedule or program specifying the required timing, illuminance and color temperature of the light across a defined treatment period. The controller then executes the light therapy by controlling the lighting assembly in such a way that it delivers the light as specified in the schedule.

In certain examples, feedback sensors may in addition be provided and the light therapy program adjusted in accordance with a closed loop configuration based on the amount of detected ambient daylight, detected patient presence or absence, and/or the duration for which a patient's eyes are open or closed.

Figure 1:
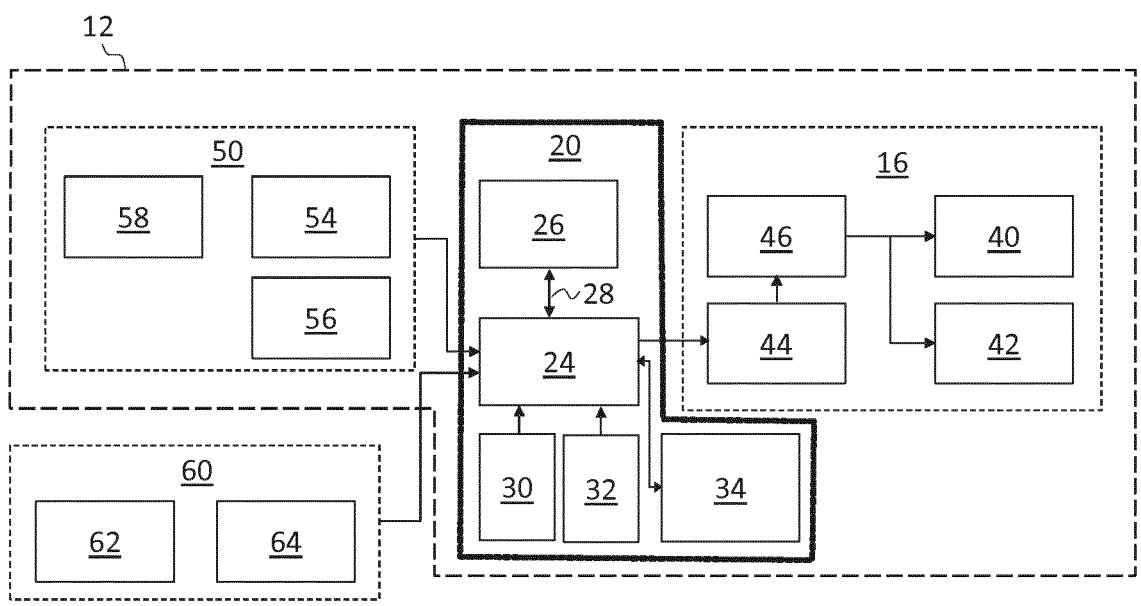
FIG. 1 is a block diagram showing an example light therapy system in accordance with an embodiment of the invention.
Figure 2:
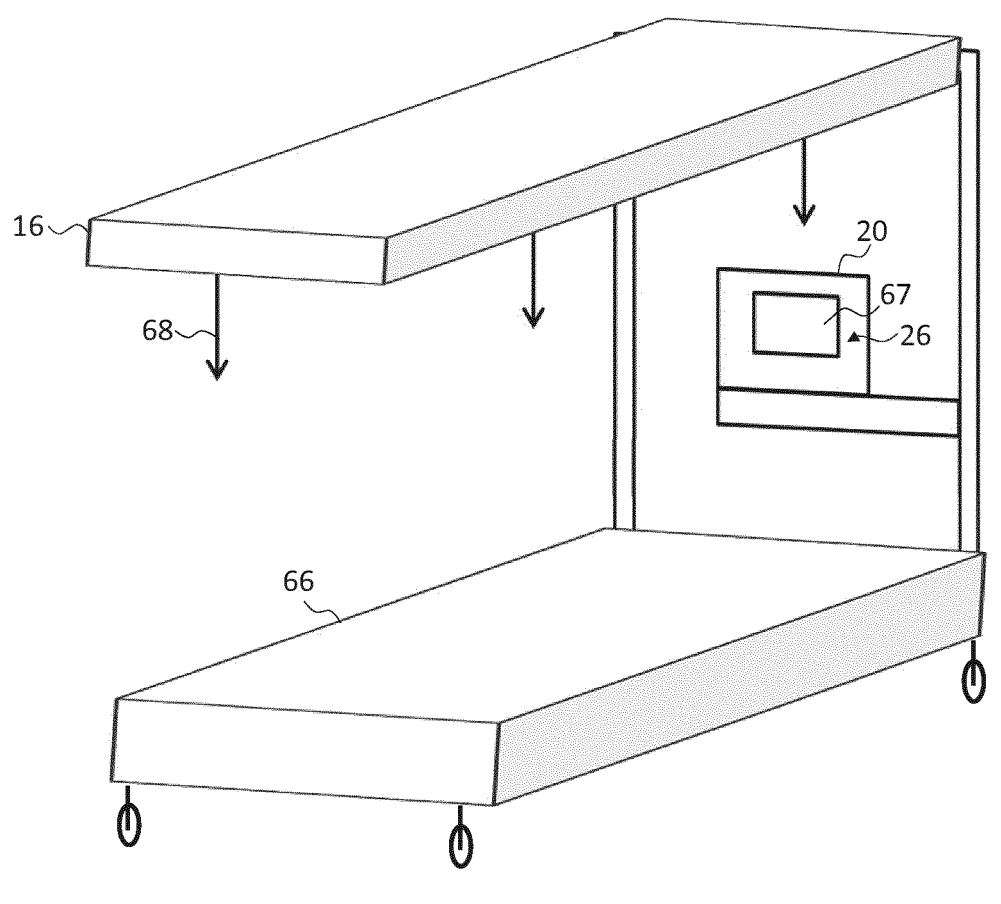
FIG. 2 schematically depicts the configuration in use of an example light therapy system according to an embodiment of the invention.

FIG. 1 shows a block diagram of an example light therapy system 12 in accordance with an embodiment of the invention. FIG. 2 schematically depicts an example physical layout of the example system 12.

The system comprises a lighting assembly 16 operable to create a light output having a controllable illuminance and color temperature. The lighting assembly is operatively coupled to a controller 24 of a light therapy control unit 20. The light therapy control unit further comprises a user interface 26 and a first data store 30, a second data store 32 and a third data store 34. The first data store 30 stores configuration and specification data relating to the lighting assembly, the second data store stores a set of melanopic weighting factors corresponding to the relative biological effect of different color temperatures of light, and the third data store comprises a set of one or more control schedule templates based upon which the controller 24 may create each control schedule. Although three data stores 30, 32, 34 are provided in the example of FIG. 1, in further examples these may for instance be combined into one data store and/or may be integrally comprised by the controller 24 or may be remote to the lighting system and communicatively linked to the controller 24.

In use, the controller 24 of the control unit 20 is adapted to receive from the user interface 26 a data input 28 indicating a target melanopic luminous exposure for administration by the lighting assembly 16. The controller is adapted to retrieve from one of the data stores (for the purposes of the present example this is assumed to be the second data store 32) a set of melanopic weighting factors corresponding to different biological sensitivities of the body to various color temperatures of light. Based upon these factors (as well as possibly other factors) the controller is adapted to create a control schedule for controlling illuminance and color temperature values of the lighting assembly over time such as to deliver in total over the course of a defined treatment period the target melanopic luminous exposure. The controller is then configured to execute this control schedule by means of suitable communication with the lighting assembly 16.

The lighting assembly for the purposes of the present example is assumed to be an LED-based lighting panel 16. This is illustrated for instance in FIG. 2, which shows the lighting assembly is use arranged above a treatment bed 66 in which a patient might lay or sit. In use, the light panel 16 emits a light output 68 downward toward the bed for delivery to a patient.

The light panel 16 for the present example is assumed to comprise two sets of LED modules 40, 42, each, in use, emitting light of a different spectral composition, and of a different color temperature. The first set of LED modules 40 is adapted to emit light of a cool color temperature (corresponding broadly to light of temperature greater than 5000 Kelvin) and the second set of LED modules 42 is adapted to emit light of a warm color temperature (corresponding broadly to light having a temperature in the range of approximately 2700-3000 K).

When the two sets of LED modules 40, 42 are activated simultaneously, a combined light output is generated, formed of a mix of light from each set. By appropriately controlling the relative light levels (i.e. power output) of each of the two sets of modules, light of a broad range of different color temperatures can be generated. For instance, by emitting the cold LED modules at greater relative power, a relatively cold light output may be created; emitting the warm LED modules at greater relative power will generate light of warmer relative color temperature.

The lighting assembly 16 further comprises a local light assembly controller 46 for controlling the relative light levels of the LED modules 40, 42 such as to create a light output of a given color temperature and a given illuminance. This is done is association with a local light assembly driver 46 which facilitates respective control of the two LED modules 40, 42 to achieve a required color temperature and illuminance. Control by the driver may be in accordance with any suitable addressing protocol including by way of example the Digital Addressable Lighting Interface (DALI) protocol.

In use, once the controller 26 has generated a control schedule suitable for delivering the target melanopic luminous exposure, the controller 26 communicates with the light assembly controller 46 to instruct it to control the LED modules 40, 42 so as to generate at appropriate times light outputs being in accordance with the created schedule.

Although LED modules are used in particular in the present example, this is not essential to the invention. The general concept of the invention simply requires a lighting assembly operable to create a light output having a controllable illuminance and color temperature. Any configuration or technical implementation of this concept will be suitable. This could include lighting assemblies comprising other forms of solid state light sources, or alternatively fluorescent or incandescent light sources for instance. Two sets of light modules 40, 42 are provided in the example of FIG. 1. However, this is again not essential. In further examples a greater or lesser number may be provided. A single lighting module may be provided operable to generate a combined light output of a configurable color temperature and illuminance.

Optionally, the system further includes an assembly 50 of sensors 54, 56, 58 for providing feedback in adjusting parameters of the light therapy schedule such as to ensure delivery of a target melanopic luminous exposure. This optional aspect will be described in greater detail below.

Optionally also, the system may be communicatively coupled with a patient data management system 60 comprising a medical record system 62 and a patient monitoring system 64. This may enable integration of the delivered light therapy with broader clinical targets and objectives for the patient as well as enabling in some examples adaptation of the therapy in accordance with certain patient-specific clinical parameters or needs (such as age or cumulative duration of stay). This optional aspect will also be described in greater detail in sections to follow.

To facilitate effective control of the lighting assembly and efficient generation of control schedules, various data sets are stored in each of the first 30, second 32, and third 34 data stores of the control unit 20, associated respectively with the lighting assembly, the melanopic weighting of different color temperatures of light, and templates for generating control schedules.

The first data store 30 preferably stores two primary data sets associated with the lighting assembly 16. Firstly, the data store 30 stores a table (or other suitable data structure) listing for all possible combinations of light levels (for instance DALI light levels) of the LED modules 40, 42, the resulting color temperature of the light generated by the lighting assembly.

Table 1 below shows (an extract of) an example such color temperature table for a lighting assembly such as in FIG. 1 having a set of warm LED modules 42 and a set of cold (white) LED modules 40. It shows that if for example the cold white LED modules are powered at a (DALI) light level of 190 and the warm white LED modules at a (DALI) light level of 65, then the resulting color temperature is 5000 Kelvin.

TABLE 1

| DALI Light level | | Color |
| Cold LED Modules | Warm LED Modules | Temperature (Kelvin) |
| --- | --- | --- |
| 0 | 255 | 2602 |
| 1 | 254 | 2635 |
| 2 | 253 | 2670 |
| . . . | . . . | . . . |
| 122 | 123 | 4002 |
| . . . | . . . | . . . |
| 190 | 65 | 5000 |
| . . . | . . . | . . . |
| 255 | 0 | 6501 |

This data set may be used by the controller 24 to provide appropriate control instructions to the lighting assembly 16 to enable generation of light outputs of particular colors.

A data set such as that of Table 1 may be generated empirically for a given lighting assembly 16, by varying the light level settings of the different LED modules 40, 42 and measuring the resultant color temperature of the combined light output. This could be implemented technically to speed up data collection, for instance by providing a controller configured to sweep rapidly through all possible combinations of light level settings and to measure the corresponding light output color temperature.

Alternatively, in some cases, a lighting assembly 16 may be provided with such a data set by the manufacturer.

Further to the color temperature table, the first data store 30 preferably also stores a table (or other data structure) listing the maximum and minimum possible illuminance of a light output which can be generated using the lighting assembly 16. This will generally be a function of the maximum and minimum illuminances of each of the component lighting modules 40, 42 of the lighting assembly. This table may, among other things, be used by the controller to ensure that control instructions provided to the lighting assembly 16 are not outside of its operational parameters. Such control instructions may lead to operational errors.

Table 2 shows an example of such an illuminance data table. In this example for instance, the table indicates that the maximum illuminance of the relevant lighting assembly 16 is 2000 Lux (and the minimum 0). Preferably, illuminance in this table indicates illuminance as measured at the location of the patient and even more preferably at the location of the patient's eye(s).

TABLE 2

| Parameter | Min | Max |
| --- | --- | --- |
| Illuminance LED Modules [Lux] | 0 (DALI = 0) | 2000 (DALI = 255) |

To improve accuracy of the delivered light therapy how-ever, preferably the data set is generated empirically in situ, since the observed color temperature may depend upon the environmental conditions in which the light therapy system is operated. Measuring the resultant color temperature for each set of light levels should preferably be done as close as possible to the likely or actual position of the patient.

Preferably, the light therapy system 12 is configured to support a range of different specific lighting assemblies. To this end, the first data store 30 preferably contains configuration data (including one of each of the above data sets) for each supported lighting assembly. At installation time, data corresponding to the correct lighting assembly may be selected by the controller (or a user), either based on automated detection by the controller of the connected lighting assembly, or based on user input provided via the user interface 26.

As discussed above, the biological effect of light upon the circadian rhythm of a patient depends upon the color temperature of the light. The controller 24 is configured to take account of these differing effects when creating a control schedule. To facilitate this, the second data store 32 stores a set of melanopic weighting factors for each possible color temperature of light. In some examples, a dedicated table may be provided for each lighting assembly 16 compatible with the system, listing weighting factors for only those color temperatures the lighting assembly is able to generate. In other examples, a single comprehensive list may be provided listing weighting factors corresponding to every possible color temperature (or at least a comprehensive range). This list might be consulted for any lighting assembly.

Table 3 below shows an extract of an example set of weighting factors. The higher the factor, the higher the biological effect. Table 3 shows for example that the melanopic factor is 0.903 if the lighting panel is operated at a color temperature of 5000 Kelvin.

TABLE 3

| Color Temperature (Kelvin) | Melanopic Weighting Factor |
| --- | --- |
| 2602 | 0.456 |
| 2635 | 0.461 |
| 2670 | 0.469 |
| . . . | . . . |
| 4002 | 0.780 |
| . . . | . . . |
| 5000 | 0.903 |
| . . . | . . . |
| 6501 | 1.035 |

Approximate values for melanopic weighting factors corresponding to color temperatures falling in between the values recited in the table may be derived by linear interpolation between neighboring data points in the table. For example, to derive an approximate weighting factor for a color temperature of 3000 K, linear interpolation may be applied between 2670 K and 4002 K.

Figure 3:
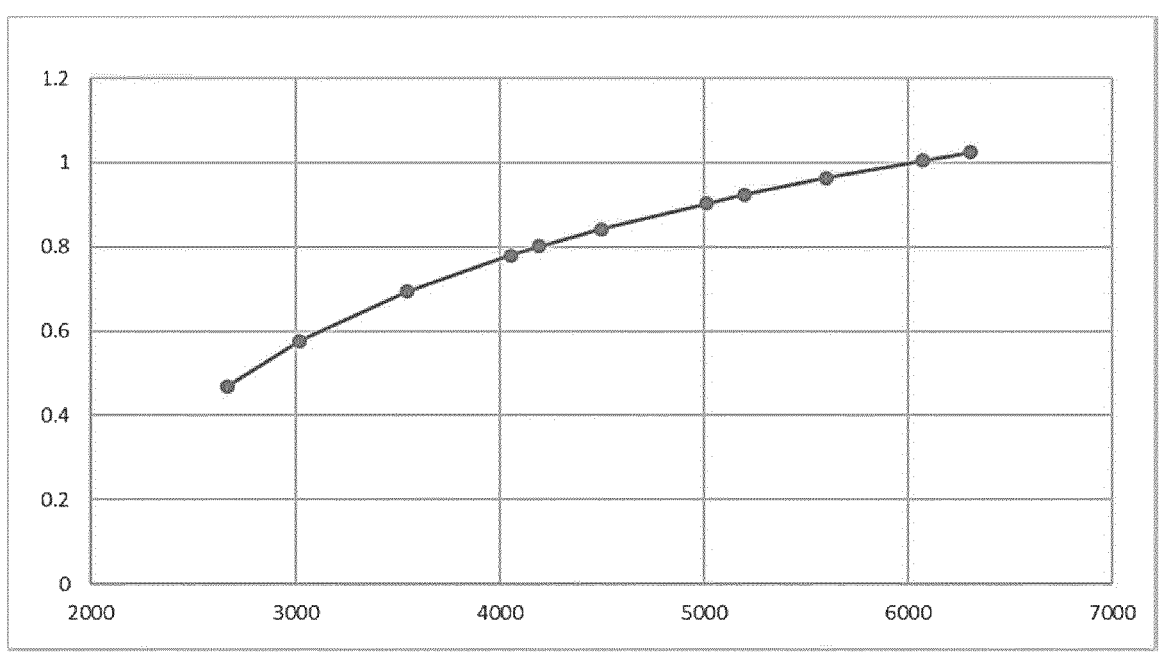
FIG. 3 depicts in graphical form an example control schedule template.

Alternatively, melanopic weighting factors for intermediate color temperatures may be determined with more accuracy using the graph shown in FIG. 3. The graph provides a curve of melanopic weighting factor (y-axis) vs color temperature (x-axis). The melanopic weighting factor for any color temperature spanned by the curve may be determined by simply reading off values from the graph.

Figure 4:
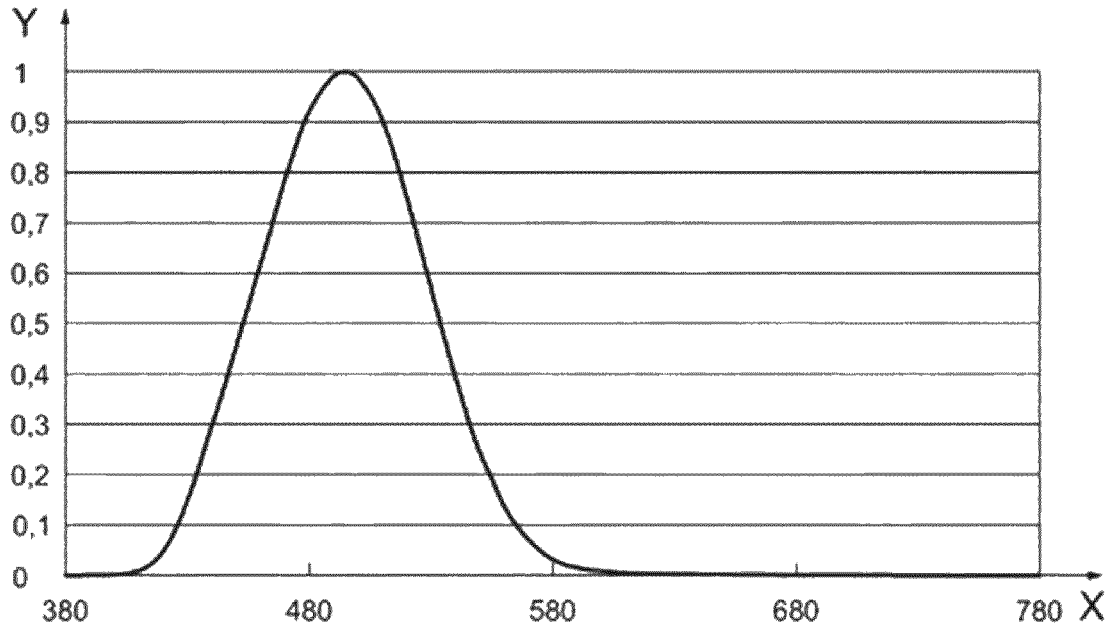
FIG. 4 is a graph showing melanopic weighting factor as a function of color temperature.

Both the values in Table 3 and the relationship illustrated in the graph have been determined based on research into the varying melanopic effects of light of differing monochromatic wavelengths. This research has showed that a clear relationship may be established between the wavelength of light and its biological effect upon the human circadian rhythm. FIG. 4 shows the trend that has been established, with the y-axis showing the relative melanopic effect and the x-axis showing wavelength (units: nm). This graph has been taken from the German Institute for Standardization (DIN) publication "DIN SPEC 5031-100: Optical radiation physics and illuminating engineering—Part 100: Melanopic effects of ocular light on human beings—Quantities, symbols and action spectra" (page 16). The values used for the graph are shown in tabular form in the same document in Appendix C (pages 27-29).

The present invention is based upon the insight that this research may be usefully applied in more realistic clinical settings by considering how these effects may manifest in more complex spectral compositions of light, in particular light of particular color temperatures. As will be well known to the skilled person, color temperature of a light source refers to the temperature of an ideal black body radiator that radiates light of comparable color to that of the light source. The black body emission spectrum of light of a given temperature is readily derivable from first principles using Planck's law of black body radiation for instance, though the spectra in the context specifically of light chromaticity have been well established independently in their own right and form part of the common general knowledge in the present field.

Using the relationship shown in the graph of FIG. 4, and the known spectral composition of light of a different color temperatures, the melanopic weighting factor for light of any color temperature may be derived from first principles by simply calculating a weighted sum of the melanopic factors of each of the spectral components of the light, weighted by their relative amplitude or intensity in the spectral composition.

As discussed above, the controller 24 of the control unit 20 is configured to receive, preferably via the user interface 26, a data input 28 indicating a target melanopic luminous exposure for administration by the lighting system 12. The controller is then configured, based on melanopic weighting factors retrieved from a data store (in the example of FIG. 1, the second data store 32), to generate a control schedule for appropriately controlling the lighting assembly 16 to deliver the target luminous exposure.

In accordance with a preferred set of embodiments, the controller 24 is adapted to generate each control schedule based on a pre-stored control schedule template. One or more suitable schedule templates may for instance be stored in a local data store. For the purposes of the example of FIG. 1, these are taken to be stored in the third data store 34 of the control unit 20.

Figure 5:
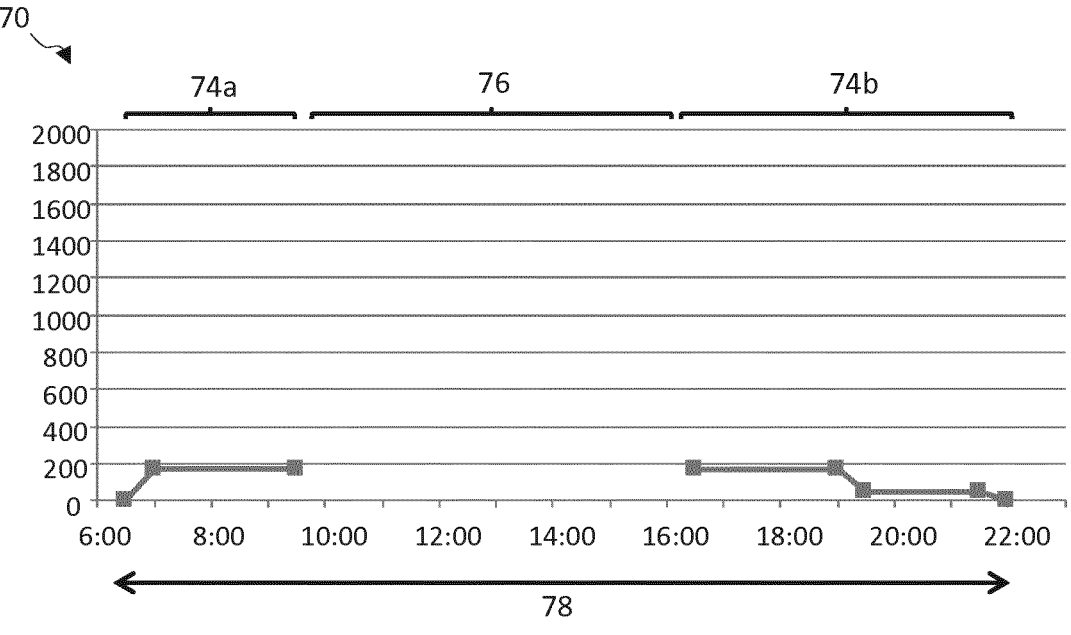
FIG. 5 is a graph showing melanopic weighting factor as a function of wavelength of light.

FIG. 5 schematically illustrates in graphical form an example control schedule template 70. The template is presented in the form of a (incomplete) line graph showing illuminance (y axis; units [Lux]) as a function of time (x axis; hours). The template comprises a fixed temporal portion 74, which is pre-configured and formed of the combination of a beginning section 74a and an end section 74b, and a configurable temporal portion 76 for generation by the controller 24. The fixed temporal portion is pre-determined and follows a fixed pattern or curve of illuminance against time. The configurable temporal portion is configurable by the controller, based upon the required melanopic luminous exposure.

Figure 6:
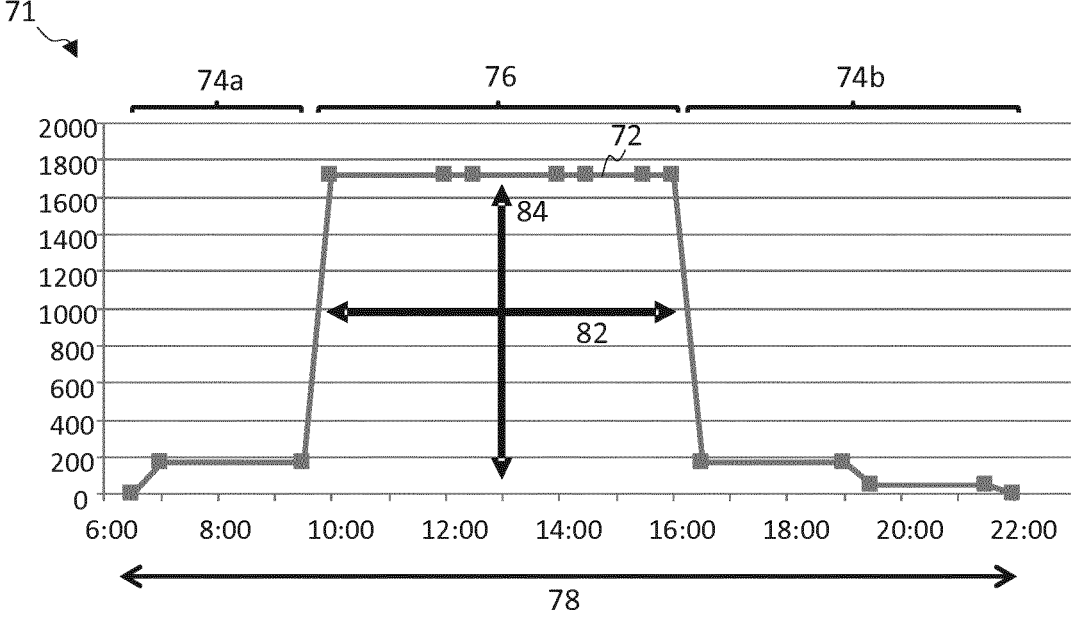
FIG. 6 depicts in graphical form an example control schedule.
Figure 7:
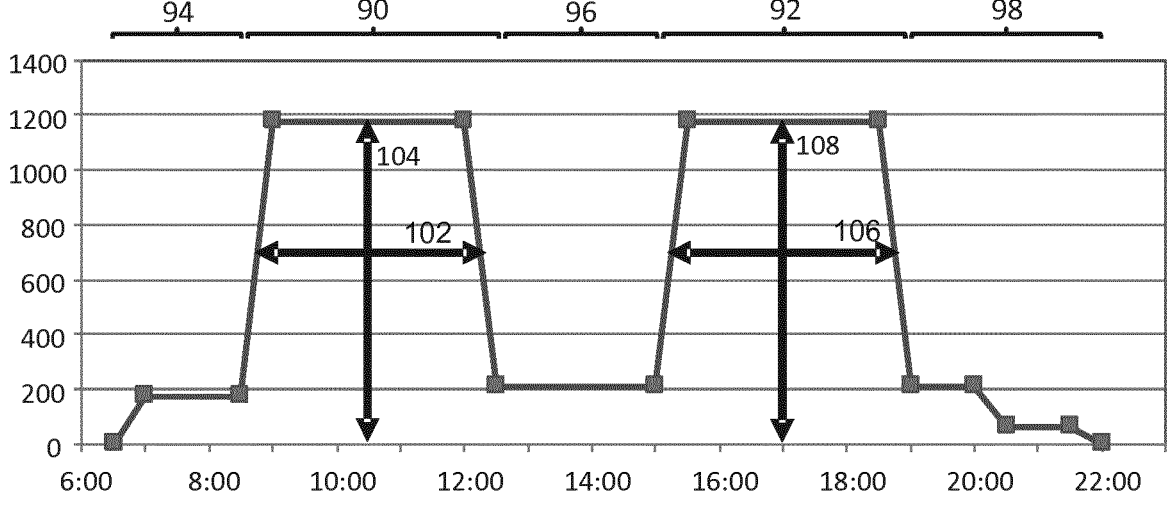
FIG. 7 depicts in graphical form a further example control schedule template.

The controller 24, upon retrieval of the template 70 generates the configurable temporal portion 76 to thereby create a full control schedule, formed of the fixed portion 74 and the configurable portion. The full schedule in this example extends for a total treatment period 78 of 16 hours, from 06:00 to 22:00. This is illustrated in FIG. 6 which shows in graphical form (at least the illuminance values of) a full control schedule 71 for the duration of the treatment period 78. The full control schedule 71 forms a continuous treatment 'curve' 72 extending from the beginning to the end of the treatment period.

As can be seen from FIG. 6, the fixed portion 74 provides a low-level baseline light output, while the configurable portion 76 provides the substantive part of the luminous exposure, comprising a light output of significantly higher illuminance than that the fixed portion. For this reason, the configurable portion may in descriptions to follow be referred to as a 'boost' portion.

When creating a control schedule 71 for controlling the lighting assembly 16, the controller 24 retrieves from the third data store 34 a control schedule template 70 such as that shown in FIG. 5 and configures the configurable temporal portion 76 such that in total over the complete treatment period 78, the target melanopic luminous exposure is delivered. In preferred examples, both a duration 82 and maximum illuminance level 84 of the configurable portion 76 are configurable. In some examples, the total duration of the treatment period 78 is fixed, such that adjusting the duration of the configurable portion results in a corresponding alteration to the total duration of the fixed portion 74. However, in further examples, the treatment period 78 may be extendable, in which case extending or reducing the duration of the configurable portion results simply in commensurate extension or reduction of the total treatment period.

The graphical representation of template 70 and completed control schedules 71 of FIGS. 5 and 6 show only variations in illuminance values (y-axis) over time. However, the schedule template 70 and completed schedule 71 also both include color temperature values, including fixed color temperature values during the fixed temporal portion 74 and configurable values during the configurable portion 76.

This is shown more clearly in Table 4 below, which shows in tabular form an example control schedule template. The table shows that during the pre-configured start and end portions 74a and 74b, illuminance and color temperature each marginally increase during the beginning section 74a and decrease during the end section 74b. In particular the illuminance linearly increases from 0 Lux at 06:30 hours to 300 Lux at 07:00 hours. The color temperature gradually increases from 2700 Kelvin to 3000 Kelvin during this time.

Blank cells in Table 4 indicate parameter values which are configurable by the controller. Upon initially retrieving the template, these values are blank, and must be calculated by the controller to deliver target melanopic luminous exposure. The thus completed template forms the full control schedule.

TABLE 4

| Start Time | End Time | Start Illuminance [Lux] | End Illuminance [Lux] | Start Color Temperature [Kelvin] | End Color Temperature [Kelvin] |
|---|---|---|---|---|---|
| 00:00 | 06:30 | 0 | 0 | 2700 | 2700 |
| 06:30 | 07:00 | 0 | 300 | 2700 | 3000 |
| 07:00 | 07:30 | 300 | 300 | 3000 | 3000 |
| 07:30 | | 300 | | 3000 | |
| | 17:30 | | 300 | | 3000 |
| 17:30 | 19:00 | 300 | 300 | 3000 | 3000 |
| 19:00 | 19:30 | 300 | 100 | 3000 | 2700 |
| 19:30 | 22:00 | 100 | 100 | 2700 | 2700 |
| 22:00 | 00:00 | 0 | 0 | 2700 | 2700 |

There will now be described in detail one example implementation of the system to create a control schedule and administer a light therapy program. This example should not be construed as limiting of the broad general scope of the invention as defined in the claims, but merely provides an illustration one possible implementation.

In accordance with at least one set of embodiments, implementation of the system 12 consists of three phases: an initial configuration phase, a light therapy prescription phase, and a light therapy execution phase.

During the initial configuration phase, a clinician or other user may configure certain boundaries or constraints for parameters of the configurable portion 76 of the control schedule template(s) 70. For example, a clinician may wish to set upper and lower limits for the duration 82 of the configurable portion 76 of the control schedule 71 and/or upper and lower limits of the illuminance 84 during the configurable portion. Table 5 below shows an example set of such constraints. The table represents an example light therapy configuration table which might be stored in one of the data stores 30, 32, 34 of the control unit 20 in which the user has by way of example indicated that the duration of the configurable portion should be constrained to between 2 to 10 hours and the maximum illuminance level to between 500 and 2000 Lux (note that 2000 Lux is in this case in any event the maximum achievable illuminance for the present example lighting assembly—see Table 2).

TABLE 5

| Parameter | Minimum | Maximum |
|---|---|---|
| Configurable Temporal Portion Duration [Hours] | 2 | 10 |
| Illuminance Level [Lux] | 500 | 2000 |

Additionally during the initial configuration phase, the controller 24 of the control unit 20 may calculate, based on the light therapy constraints set by the clinician (Table 5) and the melanopic weighting factors stored in the second data store 32 (Table 3) minimum and maximum possible melanopic luminous exposures deliverable by the lighting assembly 16 for each of a set of different light output color temperatures. These are then stored in the first data store 30 in the form of a melanopic luminous exposure table.

An (extract of) an example such table is provided by Table 6 below. It indicates for example that with a color temperature of 5000 Kelvin, the deliverable melanopic luminous exposure ranges from 903 LuxHours to 18060 LuxHours. These values are calculated from the information given in the melanopic factor table (Table 3) and the light therapy curve configuration table (Table 5). The minimum deliverable luminous exposure is 500 Lux×2 Hours=1000 Lux-Hours. The maximum luminous exposure is 2000 Lux×10 Hours=20000 LuxHours.

By then applying the relevant melanopic factor (0.903 for a color temperature of 5000 Kelvin according to Table 3) as correction factor, a color-corrected melanopic luminous exposure range is derived as indicated in Table 6. In particular, the minimum melanopic luminous exposure is 0.903×1000 LuxHours=903 LuxHours. The maximum melanopic luminous exposure is 0.903×20000 Lux-Hours=18060 LuxHours.

TABLE 6

| Color Temperature [Kelvin] | Minimum Melanopic Luminous Exposure [Lux Hours] | Maximum Melanopic Luminous Exposure [Lux Hours] |
| --- | --- | --- |
| 2602 | 456 | 9120 |
| 2635 | 461 | 9220 |
| 2670 | 469 | 9380 |
| . . . | . . . | . . . |
| 4002 | 780 | 15600 |
| . . . | . . . | . . . |
| 5000 | 903 | 18060 |
| . . . | . . . | . . . |
| 6501 | 1035 | 20700 |

Upon generation of the light therapy configuration table (Table 5) and melanopic luminous exposure table (Table 6), the initial configuration phase is complete. The light therapy prescription phase then follows.

In the light therapy prescription phase, the clinician prescribes a desired light therapy by means of the user interface 26 of the control unit 20. An example user interface is illustrated schematically in FIG. 2 which shows the control unit 20 positioned at a rear of a patient bed 66. The unit in this example comprises a display 67 which acts a user output device of the user interface. The unit also comprises a means for user input. This may be a separate keyboard or other input device for instance, or the display may be a touch display enabling user input.

Example steps for interacting with a clinician to receive a light therapy prescription may be as follows.

Firstly, the controller 24 retrieves the minimum and maximum deliverable melanopic luminous exposures from the melanopic luminous exposure table (see Table 6) stored in the first data store 30, and displays these on the display 67.

The user (e.g. clinician) may then select, using the user interface 26, a melanopic luminous exposure to be administered. This is will be the target melanopic luminous exposure. By way of example, consider that the user selects a target luminous exposure of 15600 LuxHours.

Following this, the controller 24 determines and displays the minimum and maximum possible color temperatures for light delivered by the lighting assembly, based on the selected melanopic luminous exposure. This is calculated using the stored melanopic luminous exposure table (Table 6). It can be seen from the table that a luminous exposure of 15600 LuxHours requires a color temperature of at least 4002 Kelvin.

The user may then select the preferred color temperature. By way of example, consider that the user selects a color temperature of 5000 Kelvin.

It is noted that although in the present example, the user at this stage is presented only with the option of selecting a preferred color temperature, in other examples, the controller may calculate minimum and maximum deliverable values for any one or more of the parameters: color temperature, duration 82 of the configurable portion 76 of the control schedule, and illuminance level 84 of the light output during the configurable portion. Any or all of these may be displayed to the user via the display 67, and the user given the option of selecting a preferred value for one or more of the parameters.

Returning to the present example, after receipt of a preferred color temperature value, the controller 24 then determines and displays the possible minimum and maximum durations for the configurable portion 76 of the control schedule. The possible values are determined based on the indicated target melanopic luminous exposure and preferred light color temperature, and are calculated by reference to the melanopic luminous exposure table (Table 6), the light therapy curve configuration table (Table 5), and the melanopic factor table (Table 3).

For the present example, it was assumed that a preferred color temperature of 5000 Kelvin was selected. The minimum possible duration of the configurable temporal portion 76 is calculated by assuming that the maximum illuminance level of 2000 Lux is applied uniformly throughout this temporal portion: 15600 LuxHours/(2000 Lux*0.903)=8.6 Hours.

The maximum possible duration of the configurable temporal portion 76 is calculated by assuming that the minimum illuminance level of 500 Lux is applied uniformly throughout the temporal portion: 15600 LuxHours/(500 Lux*0.903) =34.6 hours. However, since in the initial configuration phase, the user (in this example) constrained the maximum duration of the configurable temporal portion of the control schedule to 10 hours (see Table 5), the maximum duration is capped at 10 hours.

The controller may also concurrently at this stage determine and display the minimum and maximum possible illuminance levels for the configurable portion of the control schedule. These are based again on the target melanopic luminous exposure and the received preferred color temperature, and are calculated using the melanopic luminous exposure table (Table 6), the light therapy configuration table (Table 5), and the melanopic weighting factor table (see Table 3). For simplicity of calculation, in accordance with at least some examples, the controller may create the control schedule such that a uniform illuminance of light is delivered throughout the duration 82 of the configurable portion 76 of the control schedule 71.

The minimum illuminance level is calculated by assuming that the maximum duration 82 for the configurable temporal portion 76 of 10 hours is applied: 15600 LuxHours/(10 hours*0.903)=1728 Lux. The maximum illuminance level is calculated by assuming that the minimum duration of 2 hours is applied: 15600 LuxHours/(2 hours*0.903)=8638 Lux. However, since the user configured the maximum illuminance level to be 2000 Lux, the maximum is capped at 2000 Lux.

The thus calculated maximum and minimum possible illuminance levels and durations of the configurable portion 76 of the control schedule 71 are displayed using the display 67 of the user interface 26. The user may then input either a preferred duration or a preferred illuminance level. If the user inputs a preferred duration, then the controller calculates a corresponding appropriate illuminance level for delivering the target melanopic luminous exposure, based on the input duration. If the user inputs a preferred illuminance level, the controller likewise calculates a corresponding appropriate duration for delivering the target luminous exposure, based on the input illuminance level.

It is noted that although in the present example, the controller is configured to concurrently calculate and display maxima and minima for both the configurable portion duration and illuminance level, in further examples, only one of these may be determined and displayed. Which is calculated and displayed may be set by a user as part of the initial configuration phase in accordance with one or more examples.

For the purposes of the present example, it is assumed for illustration that the user selects a preferred duration for the configurable portion 76 of the control schedule 71 of 9 hours. The required illuminance level may then can be calculated as follows: 15600 LuxHours/(9 hours*0.903) =1920 Lux. This assumes that a uniform illuminance level is to be applied throughout the duration 82 of the configurable portion 76 of the schedule.

Based on the totality of the input preferred parameter values and the calculated parameter values, and based also on the fixed parameter values during the fixed temporal portions 74a, 74b of the control schedule template 70, the controller 24 creates a control schedule for the illuminance and color temperature values of the lighting assembly 16 across the duration of the treatment period 78. The full created schedule in accordance with the illustrative values presented in the above example is shown by Table 7 below.

TABLE 7

| Start Time | End Time | Start Illuminance [Lux] | End Illuminance [Lux] | Start Color Temperature [Kelvin] | End Color Temperature [Kelvin] |
|---|---|---|---|---|---|
| 00:00 | 06:30 | 0 | 0 | 2700 | 2700 |
| 06:30 | 07:00 | 0 | 300 | 2700 | 3000 |
| 07:00 | 07:30 | 300 | 300 | 3000 | 3000 |
| 07:30 | 18:00 | 300 | 1920 | 3000 | 5000 |
| 08:00 | 17:00 | 1920 | 1920 | 5000 | 5000 |
| 17:00 | 17:30 | 1920 | 300 | 5000 | 3000 |
| 17:30 | 19:00 | 300 | 300 | 3000 | 3000 |
| 19:00 | 19:30 | 300 | 100 | 3000 | 2700 |
| 19:30 | 22:00 | 100 | 100 | 2700 | 2700 |
| 22:00 | 00:00 | 0 | 0 | 2700 | 2700 |

Having thus created the control schedule of Table 7 for the light therapy, the controller 24 is configured to determine for each color temperature of light throughout the control schedule appropriate power levels of each of the LED modules 40, 42 of the lighting assembly 16 necessary to achieve those light color temperatures. These power levels are preferably determined based on an appropriate color temperature table pre-stored in the first data store 30 (for the example lighting assembly in the system of FIG. 1, see Table 1 above).

As noted above, the power levels may in accordance with one or more examples be codified using the DALI addressing protocol. Table 8 shows an example such set of (DALI) power levels for the cold white 40 and warm 42 LED modules of the lighting assembly 16 of the example system of FIG. 1, based on the color temperature values of the example control schedule of Table 7 above. The color temperature table of Table 1 has been used to calculate the necessary DALI light levels for each light color temperature.

TABLE 8

| Start Time | End Time | Start (DALI) Light Level - Cold White LED Modules | End (DALI) Light Level - Cold White LED Modules | Start (DALI) Light Level - Warm LED Modules | End (DALI) Light Level - Warm LED Light Modules |
|---|---|---|---|---|---|
| 00:00 | 06:30 | 0 | 0 | 0 | 0 |
| 06:30 | 07:00 | 0 | 42 | 0 | 213 |

TABLE 8-continued

| Start Time | End Time | Start (DALI) Light Level - Cold White LED Modules | End (DALI) Light Level - Cold White LED Modules | Start (DALI) Light Level - Warm LED Modules | End (DALI) Light Level - Warm LED Light Modules |
|---|---|---|---|---|---|
| 07:00 | 07:30 | 42 | 42 | 213 | 213 |
| 07:30 | 18:00 | 42 | 190 | 213 | 65 |
| 08:00 | 17:00 | 190 | 190 | 65 | 65 |
| 17:00 | 17:30 | 190 | 42 | 65 | 213 |
| 17:30 | 19:00 | 42 | 42 | 213 | 213 |
| 19:00 | 19:30 | 42 | 2 | 213 | 253 |
| 19:30 | 22:00 | 2 | 2 | 253 | 253 |
| 22:00 | 00:00 | 0 | 0 | 0 | 0 |

As stated, the set of DALI light levels of Table 8 above have been calculated based on the color temperature table of Table 1. However, the values of this table were calculated based upon the assumption that the lighting assembly 16 is operating a maximum illuminance, i.e. 2000 Lux (see Table 2 above).

For the present example, the illuminance is lower than the maximum of 2000 Lux, and hence a correction must be applied to the power levels of Table 8.

To this end, the controller 24 may calculate the ratio between the illuminance level during the configurable portion 76 of the control schedule 71 and the maximum illuminance of the lighting assembly during this time period. This is then applied to the DALI light level values of Table 8 corresponding to the configurable temporal portion as a correction factor. The resulting final DALI light level schedule is shown in Table 9 below.

TABLE 9

| Start Time | End Time | Start (DALI) Light Level - Cold White LED Modules | End (DALI) Light Level - Cold White LED Modules | Start (DALI) Light Level - Warm LED Modules | End (DALI) Light Level - Warm LED Light Modules |
|---|---|---|---|---|---|
| 00:00 | 06:30 | 0 | 0 | 0 | 0 |
| 06:30 | 07:00 | 0 | 6 | 0 | 32 |
| 07:00 | 07:30 | 6 | 6 | 32 | 32 |
| 07:30 | 18:00 | 6 | 182 | 32 | 62 |
| 08:00 | 17:00 | 182 | 182 | 62 | 62 |
| 17:00 | 17:30 | 182 | 6 | 62 | 32 |
| 17:30 | 19:00 | 6 | 6 | 32 | 32 |
| 19:00 | 19:30 | 6 | 0 | 32 | 13 |
| 19:30 | 22:00 | 0 | 0 | 13 | 13 |
| 22:00 | 00:00 | 0 | 0 | 0 | 0 |

For the present example, during the configurable temporal portion 76, the illuminance level was set at 1920 Lux. The correction factor for values during this portion of the schedule is therefore 1920 Lux/2000 Lux=0.96. The resulting DALI light level for the cold white LED modules 40 during the configurable portion of the schedule is 190*0.96=182. The resulting DALI light levels for the warm LED modules 42 during the configurable portion is 65*0.96=62.

The same correction process for the fixed temporal portion 74 of the control schedule must also be performed. The illuminance during this portion varies, and is in all cases significantly lower than the illuminance throughout the configurable temporal portion 76. Calculation of the correction factors for every illuminance level during the fixed portion will not be exhaustively iterated here, since it will be obvious the skilled person how to perform the necessary calculations. By way of a single example, the illuminance at 07:00 hours is 300 Lux. The correction factor is thus 300/2000=0.15. Applying this correction factor to the DALI light levels of Table 8 for 07:00 yields a value of 6 (=42*0.15) for the cold white LED modules 40 and 32 (=213*0.15) for the warm LED modules 42.

In accordance with at least some examples, the corrected DALI light levels for the fixed temporal portions of each control schedule template 70 may be pre-calculated and stored in the first data store 30 for each lighting assembly compatible with the lighting system. This is possible since the illuminance levels during the fixed portion are pre-set. Pre-storing the corrected DALI light levels for each control schedule template may increase processing efficiency of the system in creating each complete control schedule 71.

Once the corrected light level schedule is derived, as in the example of Table 9, this may be stored, for example in the third data store 34.

The light therapy prescription phase is then complete. The final phase is the light therapy execution phase in which the created control schedule is executed.

In accordance with this phase, the controller 24 is configured to control the lighting assembly 16 to vary the light levels of the LED modules 40, 42 in accordance with the derived light level schedule (Table 9).

To this end, the controller 24 is adapted to perform the following series of steps recurrently (i.e. at regular time intervals):

1. Retrieve or read the stored light level schedule (Table 9).
2. Determine the current time.
3. Identify the row of the light level schedule corresponding to the current time and thus identify the required DALI light level for the cold white LED Modules 40 and the warm white LED Modules for the current time. In the case that the current time is between time points of the light level schedule, the controller may be adapted to assume that the light level should linearly increase or decrease between time points. For example, with reference to Table 8, if the time were 07:45, the light level for the cold white LED modules 40 would be set half way between 6 and 182, i.e. at a level of 94. The warm LED modules 42 would be set halfway between 32 and 62, i.e. at 47.
4. Communicate the required light level for each of the LED modules 40, 42 for the given point in time to the lighting assembly controller 44.

The lighting assembly controller 44 then instructs the driver module 46 of the lighting assembly in accordance with the received required light level. The driver module (in the present case a DALI driver module) then controls the LED modules 40, 42 accordingly.

The controller may be adapted to repeat the above series of steps by way of non-limiting example, every 10 seconds, or every 30 seconds, or every 5 seconds, depending upon how closely the different time points of the control schedule are spaced.

In accordance with one or more embodiments, the lighting system 12 may further comprise one or more sensors for providing feedback in controlling the lighting assembly or in creating the control schedule 71. By way of example, the example lighting assembly of FIG. 1 comprises an assembly 50 of such sensors, which include a presence sensor 54, an eye status sensor 56 and a light level sensor 58. The sensors may for example facilitate a feedback loop, wherein the control schedule may be adjusted in accordance with readings from the sensor(s). Other example lighting systems 12 may comprise none of these sensors or may comprise a subset of one or more of these sensors, as well as optionally further additional or alternative sensors. More than one of any given type of sensor may be provided.

A presence sensor 54 in accordance with examples may be provided operatively coupled with the controller 24 and arranged in use to detect whether a patient is present within the vicinity of the lighting assembly. The presence sensor may be adapted to detect the presence or absence of a user (such as a patient) in a light output path of the lighting assembly 16. The trajectory of the light output path of the lighting assembly may be known in advance (for instance where the system has a fixed spatial arrangement), in which case the presence sensor can be arranged having a fixed field of view directed toward the projection location of the lighting assembly. For example, with reference to FIG. 2, it would be known that the light output path of the lighting arrangement 16 is towards the patient bed 66. In this case, a presence sensor may be arranged having a field of view directed toward at least a sub-region of the bed.

The controller may be adapted to pause execution of the control schedule upon detecting that the patient is absent, and to continue the control schedule upon detecting that the patient has returned. This would ensure that portions of the scheduled treatment are not missed and the patient receives the full prescribed melanopic luminous exposure.

Alternatively, the controller 24 may be adapted to adjust a duration of, and/or the illuminance and/or color temperature of, the light output during at least a configurable temporal portion of the control schedule based on readings from the sensor in order to ensure delivery of the target luminous exposure. The schedule 71 may be extended or the illuminance increased during the configurable portion 76 such that the patient, assuming they remain present for the remainder of the adjusted schedule, receives the full target melanopic luminous exposure.

In accordance with one or more examples, the system may include an eye status sensor 56 adapted to detect whether the eyes of a patient are open or closed. This may be an eye tracking sensor, or may be camera or may be a different kind of optical sensor or may be any other form of sensor suitable for the stated purpose, such as ultrasound or acoustic sensor. The sensor may be operable to detect only changes in eye status (i.e. not the absolute status) and so may need calibrating. Alternatively, the sensor may be operable to detect at any given moment whether a patient's eyes are open or closed.

The controller may be configured to adjust the control schedule based on readings from the sensor. For example, the controller may pause execution of the control schedule upon detection that a patient's eyes are closed and continue execution of the control schedule upon detection that the patient's eyes have re-opened.

Alternatively, at least a configurable portion 76 of the control schedule 71 may be extended in duration, or an illuminance level increased during the configurable portion, to compensate for time that a patient's eyes are detected as being closed.

In particular, the controller 24 may be adapted to adjust a duration of, and/or the illuminance and/or color temperature of, the light output during at least a configurable temporal portion of the control schedule based on the readings from the sensor in order to ensure delivery of the target luminous exposure.

The controller 24 may be adapted to calculate, based on readings from the eye status sensor over a defined sensing period, an aggregate time period for which a user's eyes have been closed, and to extend the duration of at least a configurable temporal portion of the control schedule by said aggregate time period.

Additionally or alternatively to readings from an eye sensor, the controller 24 may optionally be adapted to communicate with an associated patient monitoring system. The patient monitoring system may store or otherwise be adapted to provide to the controller information concerning other treatment or medication being administered to the patient or other physiological parameters of the patients. An example patient monitoring system is illustrated schematically in FIG. 1.

According to one or more examples, the system may comprise a light sensor for detecting a level of light proximal to or at the position of a patient to whom the light therapy is to be administered. Preferably, the sensor is positioned or adapted to sense a light level at a position proximal to the patient's eye. In accordance with some examples, the controller 24 may be adapted to increase the illuminance of the light output of the lighting assembly 16 in response to detection that the light level at the patient's eye is lower than that specified in the control schedule for the given moment in time, and vice versa to decrease the light level if the measured level is higher than the expected level for that time. In the latter case, reduction of the illuminance may avoid an overdose of light which may be harmful for the patient, or may affect the effectiveness of the treatment. The sensor allows the illuminance of the lighting assembly to be adjusted according to environmental light levels for example, so that large amounts of external light can be compensated for by lowering the illuminance of the lighting assembly.

According to examples more generally, the controller may be adapted to adjust a duration of, and/or the illuminance and/or color temperature of, the light output during at least a configurable temporal portion of the control schedule based on readings from the sensor, in order to ensure delivery of the target luminous exposure, and optionally wherein the light level sensor is arranged proximal to a user's eye or eyes.

In accordance with one or more examples, the light therapy system 12 may include all three of the above described sensors. A combination of all three may enable the system to derive an approximate measure of the actual melanopic luminous exposure received by the patient. The three sensors together are able to account for moments of absence of the patient, as well as moments at which the patient is present but their eyes are closed, as well as a measured level of the light being received at the position of the patient.

Such a combination of parameters enables more accurate delivery of a required target melanopic luminous exposure. For instance, as noted above, the therapy schedule may be adjusted in dependence upon the readings from the sensors such that the target melanopic exposure may be more accurately delivered.

In the example of FIG. 1 above, the lighting assembly 16 was taken to be a light panel comprising two sets of LED modules: cold white LED modules, and warm LED modules. However, in accordance with further examples, a different lighting assembly may be used. A lighting assembly may be used comprising only a single type of LED module (e.g. only cold or only warm light). A lighting assembly may be used comprising more than two types of LED modules, for example, three or four or more than four (e.g. cold, warm and medium white LED modules or a combination of different color LEDs).

Using more LED modules may enable a richer or broader range of light color temperatures to be achieved. This may provide a greater choice to patients as to the particular light color they would prefer, or may provide a greater range of clinical options to the clinician where the color of the light is a clinical factor. Additionally, since the melanopic effect of the light is dependent upon the color, extending the range of colors available may improve the precision with which a desired melanopic luminous exposure can be delivered, or provide greater configuration options for providing a given luminous exposure.

The biological effect of light on the entrainment ("melanopic effect") depends on the length of the light exposure, the intensity of the administered light (i.e. the illuminance) and the color temperature of the light. It is also important to note that light has only an effect on the circadian rhythm if it is actually received by the photoreceptors in the eye. Therefore, the effect of light depends also on the proportion of time that the eyes are open or closed and the transmittance of the eye lens. It is known that eye lens transmittance decreases with increasing age.

Accordingly, the control schedule 71 may be adapted in accordance with one or more examples in dependence upon the age of the patient. For example, the light level values of the light level schedule of Table 9 or the illuminance values of the control schedule of Table 7 may be adjusted by application of an appropriate age correction factor. The age correction factors may rise for increasing age, so as to increase the applied illuminance for older patients. Similarly, the correction factors may be configured to reduce the applied illuminance for younger patients having a greater lens transmissivity.

An example set of age correction factors is shown in Table 10 below.

TABLE 10

| Patient Age | Age Correction Factor |
| --- | --- |
| 1 | 0.11 |
| 2 | 0.11 |
| 3 | 0.12 |
| . . . | . . . |
| 50 | 0.53 |
| . . . | . . . |
| 75 | 100 |
| . . . | . . . |
| 100 | 2.14 |

In accordance with one or more examples, the age of the patient may be retrieved from a patient data management system to which the controller is communicatively linked. This is illustrated in FIG. 1 which shows an optional patient data management system 60 comprising an electronic medical record system 62 and patient monitoring system 64. The patient data management system may be external to the light therapy system 12, and simply communicatively linked with the controller 24. The ages of patients may be stored in the electronic medical record system 62.

The patient monitoring system 64 may in accordance with one or more examples be adapted to store and/or monitor information concerning other ancillary treatments being administered to the patient or other physiological parameters of the patient being monitored. This information may be used in addition to or instead of data provided by any sensors and/or information retrieved from the electronic medical record system 62.

For example, the patient monitoring system 64 may provide information about the current sedation level and/or the sleep stage of the patient. If the patient is deeply sedated or in a deep sleep phase, then this provides an indication, independent of any eye status sensor data, that the eyes of the patient may be closed. Thereby data from the patient monitoring system may in examples be used as an alternative or complement for example to readings from the eye status sensor described above. This data may then be used in a similar way to that described above, to adapt the therapy control schedule 71 in order better to ensure delivery of the target melanopic luminous exposure.

Additionally or alternatively, according to one or more examples, the control schedule 71 may be adjusted in accordance with a cumulative duration of a patient's stay. In particular, a clinician may wish the applied light therapy to change depending upon how long a patient has been staying within the clinical environment (e.g. hospital). There may accordingly be applied a 'length of stay correction factor' to the light levels or illuminance levels of the control schedule, the factor increasing depending upon the total amount of time that a patient has been in admittance within a hospital or clinic.

A clinician might decide for example to reduce the illuminance level during the configurable portion of the control schedule for the first day in a hospital unit (e.g. ICU), and then return the illuminance levels to normal thereafter. The clinician may furthermore decide to gradually decrease the administered light levels from the 5th day onwards, on the assumption that the circadian rhythm of the patient has, after this length of time, been restored. An example set of such correction factors is illustrated in Table 12 below. The cumulative length of stay of the patient may be retrieved from a communicatively linked patient data management system 60.

TABLE 11

| Cumulative Length of Stay [Days] | Correction Factor |
|---|---|
| 1 | 0.75 |
| 2 | 1.00 |
| 3 | 1.00 |
| 4 | 1.00 |
| 5 | 0.90 |
| 6 | 0.80 |
| >6 | 0.75 |

In examples described above, an example control schedule template 70 was presented comprising a single configurable temporal portion 76 surrounded at either end by a fixed temporal portion 74 being split into two sections 74a, 74b. In accordance with further examples however, different control schedule templates may instead be used. In particular, there may be provided stored in the third data store 34 one or more control schedule templates which include a plurality of configurable temporal portions. An example is shown in graphical form in FIG. 7. The example comprises two configurable portions 90, 92, these being separated by a set of intermediate fixed temporal portions 94, 96, 98. Each of the configurable portions has a separately configurable duration 102, 106 and maximum illuminance level 104, 108. For the purposes of illustration, the configurable portions are shown completed in FIG. 7, although it is to be understood that these portions would in fact be absent in the true template, with the controller adapted to complete them.

In accordance with any example, the fixed temporal portion or portions of the control schedule template, where such a template is used, may take any particular trend or pattern. It is preferred that the average illuminance during the fixed portion(s) is lower than the average illuminance during any of the configurable portions.

Although in examples above, the control schedule is created by the controller 24 based upon a control schedule template 70, in alternative examples, no such template may be used. Illuminance levels of the schedule throughout the duration of the treatment period 78 are set by the controller such in total over the treatment period, the target melanopic luminous exposure is delivered by the lighting arrangement.

As discussed above, embodiments make use of a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A light therapy system, comprising:
   a lighting assembly operable to create a light output having a controllable illuminance and color temperature; and
   a controller, operatively coupled to the lighting assembly, and adapted to:
   receive a data input indicating a target melanopic luminous exposure for administration by the lighting assembly;
   retrieve from a data store one or more melanopic weighting factors corresponding to a relative melanopic effect of different color temperatures of light;
   create, based on the one or more melanopic weighting factors and based on a pre-stored schedule template including a fixed temporal portion, a control schedule for controlling the illuminance and color temperature values of the lighting assembly over time such as to deliver in total over a defined treatment period the target melanopic luminous exposure; and control the lighting assembly in accordance with the control schedule.

2. The light therapy system as claimed in claim 1, wherein the controller is adapted to further receive color preference data indicating one or more preferred color temperature values, and to create the control schedule such that the color temperature of the light output, for at least a portion of the treatment period, has the one or more preferred color temperature values.

3. The light therapy system as claimed in claim 1, wherein the pre-stored schedule template also includes a configurable temporal portion, the controller being adapted to determine the configurable temporal portion and wherein the fixed temporal portion and the configurable temporal portion together are configured to deliver the target melanopic luminous exposure.

4. The light therapy system as claimed in claim 3, wherein the controller is adapted to create the control schedule such that an average illuminance level during the configurable temporal portion is higher than an average illuminance level during the fixed temporal portion.

5. The light therapy system as claimed in claim 3, wherein the pre-stored schedule template includes a plurality of configurable temporal portions, being separated by a plurality of intermediate fixed temporal portions.

6. The light therapy system as claimed in claim 1, wherein the controller is adapted to further retrieve from the data store an indication of an upper and lower limit for the illuminance of the light output during the treatment period and an indication of an upper and lower limit for a duration of at least a configurable temporal portion of the treatment period, and to create at least a configurable temporal portion of the control schedule in accordance with the illuminance and duration values.

7. The light therapy system as claimed in claim 6, further comprising:

a user input device for receiving said data input indicating the target melanopic luminous exposure; and a user output device, wherein, in advance of receiving said target melanopic luminous exposure, the controller is adapted to:

determine, based upon said upper and lower limits for the illuminance and duration values, a maximum and minimum melanopic luminous exposure deliverable using the lighting assembly for each of a set of light color temperatures; and control the user output device to communicate the maximum and minimum melanopic luminous exposure deliverable using the lighting assembly for each of the set of light color temperatures.

8. The light therapy system as claimed in claim 6, further comprising:

a user input device for receiving said data input indicating the target melanopic luminous exposure; and a user output device, wherein the controller is further adapted to:

determine, based on the upper and lower limits for the duration and illuminance, maximum and minimum values of at least one of the following parameters sufficient to deliver the target melanopic luminous exposure:

color temperature of the light output during the at least a configurable temporal portion of the control schedule, duration of the at least the configurable temporal portion of a control schedule, and illuminance level of the light output during the at least a configurable temporal portion of the control schedule;

control the user output device to communicate the determined maximum and minimum values;

receive from the user input device a data input indicating a preferred value for one or more of said parameters; and create the control schedule such that the light output, for at least a portion of the treatment period, is consistent with said preferred value.

9. The light therapy system as claimed in claim 1, wherein the data store is comprised by the controller or wherein the data store is remote from the light therapy system.

10. The light therapy system as claimed in claim 1, wherein the lighting assembly comprises a plurality of light sources each having a respective spectral emission profile, and wherein control of the color temperature of the light output comprises determining, based on pre-stored configuration data, light levels for each of said plurality of light sources.

11. The light therapy system as claimed in claim 1 further comprising:

an eye status sensor for detecting whether eyes of a user are open or closed, the eye status sensor being operatively coupled with the controller, and the controller being adapted to adjust a duration of, and/or the illuminance and/or color temperature of, the light output during at least a configurable temporal portion of the control schedule based on readings from the eye status sensor in order to ensure delivery of the target luminous exposure; and optionally wherein the controller is adapted to calculate, based on the readings from the eye status sensor over a defined sensing period, an aggregate time period for which a user's eyes have been closed, and to extend the duration of the at least a configurable temporal portion of the control schedule by said aggregate time period.

12. The light therapy system as claimed in claim 1, further comprising:

a presence sensor, operatively coupled with the controller and arranged in use to detect a presence or an absence of a user within a light path of the lighting assembly, and wherein the controller is adapted to adjust a duration of, and/or the illuminance and/or color temperature of, the light output during at least a configurable temporal portion of the control schedule based on readings from the presence sensor in order to ensure delivery of the target luminous exposure.

13. The light therapy system as claimed in claim 1, further comprising a light level sensor, arranged to detect a light level proximal to a user, and wherein the controller is adapted to adjust a duration of, and/or the illuminance and/or color temperature of, the light output during at least a configurable temporal portion of the control schedule based on readings from the sensor, in order to ensure delivery of the target luminous exposure, and optionally wherein the light level sensor is arranged proximal to a user's eye or eyes.

14. The light therapy system as claimed in claim 1, wherein the controller is further adapted to:

retrieve from the data store an indication of an age of a user;

retrieve from the data store a set of age weighting factors, being based on average sensitivity to light of users of different ages; and adjust a duration of, and/or the illuminance and/or color temperature of, the light output during at least a configurable temporal portion of the control schedule based on the retrieved age and retrieved weighting factors in order to ensure delivery of the target luminous exposure.

15. A light therapy method for controlling a lighting assembly to deliver a target melanopic luminous exposure, the lighting assembly being operable to create a light output having a controllable illuminance and color temperature, and the method comprising:

receiving a data input indicating a target melanopic luminous exposure for administration by the lighting assembly;

retrieving from a data store one or more melanopic weighting factors corresponding to a relative melanopic effect of different color temperatures of light;

creating, based on the one or more melanopic weighting factors and based on a pre-stored schedule template including a fixed temporal portion, a control schedule for controlling the illuminance and color temperature values of the lighting assembly over time such as to deliver in total over a defined treatment period the target melanopic luminous exposure; and controlling the lighting assembly in accordance with the control schedule.

16. The method as claimed in claim 15, further comprising:

receiving color preference data indicating one or more preferred color temperature values; and creating the control schedule such that the color temperature of the light output, for at least a portion of the treatment period, has the one or more preferred color temperature values.

17. The method as claimed in claim 15, wherein the pre-stored schedule template further comprises a configurable temporal portion, and the method further comprises determining the configurable temporal portion, and wherein the fixed temporal portion and the configurable temporal portion together are configured to deliver the target melanopic luminous exposure.

18. The method as claimed in claim 17, further comprising to creating the control schedule such that an average illuminance level during the configurable temporal portion is higher than an average illuminance level during the fixed temporal portion.

19. The method as claimed in claim 17, wherein the pre-stored schedule template includes a plurality of configurable temporal portions, being separated by a plurality of intermediate fixed temporal portions.

20. The method as claimed in claim 15, wherein the controller is adapted to further retrieve from the data store an indication of an upper and lower limit for the illuminance of the light output during the treatment period and an indication of an upper and lower limit for a duration of at least a configurable temporal portion of the treatment period, and to create at least a configurable temporal portion of the control schedule in accordance with the illuminance and duration values.

* * * * *